United States Patent
Shimokawa et al.

(10) Patent No.: US 9,993,194 B2
(45) Date of Patent: Jun. 12, 2018

(54) SLEEPINESS CALCULATION DEVICE

(71) Applicant: PIONEER CORPORATION, Tokyo (JP)

(72) Inventors: Hirofumi Shimokawa, Saitama (JP); Chihiro Hirose, Saitama (JP); Mitsuo Yasushi, Saitama (JP)

(73) Assignee: PIONEER CORPORATION, Tokyo (JP)

( * ) Notice: Subject to any disclaimer, the term of this patent is extended or adjusted under 35 U.S.C. 154(b) by 0 days. days.

(21) Appl. No.: 15/561,603

(22) PCT Filed: Mar. 26, 2015

(86) PCT No.: PCT/JP2015/059380
§ 371 (c)(1),
(2) Date: Sep. 26, 2017

(87) PCT Pub. No.: WO2016/151842
PCT Pub. Date: Sep. 29, 2016

(65) Prior Publication Data
US 2018/0064387 A1    Mar. 8, 2018

(51) Int. Cl.
*A61B 5/00* (2006.01)
*A61B 5/18* (2006.01)
(Continued)

(52) U.S. Cl.
CPC .............. *A61B 5/4809* (2013.01); *A61B 5/18* (2013.01); *A61B 5/4812* (2013.01);
(Continued)

(58) Field of Classification Search
CPC ....... A61B 5/4809; A61B 5/18; A61B 5/4812; A61B 5/024; A61B 5/1103; A61B 5/6893; G06K 9/00845; B60W 40/08
See application file for complete search history.

(56) References Cited

U.S. PATENT DOCUMENTS 7,397,382 B2 * 7/2008 Ikegami ............ A61B 5/02416
340/575
9,456,770 B2  10/2016 Fujita et al.
(Continued)

FOREIGN PATENT DOCUMENTS

JP          3252586     2/2002
JP      2008-035964    2/2008
(Continued)

OTHER PUBLICATIONS

International Search Report, PCT/JP2015/059380, dated Jun. 23, 2015.

*Primary Examiner* — Sisay Yacob
(74) *Attorney, Agent, or Firm* — Young & Thompson

(57) ABSTRACT

A sleepiness calculation device is provided. In a smartphone, I/F obtains heart rate of the subject measured by a heartbeat sensor and measurement time, determines active state of a subject in the state discriminant section, and send it to a server. Next, in the server, a correction section obtains sleepiness baseline heart rate from a sleepiness baseline heart rate table storing sleepiness baseline heart rate of the subject for each active state according to an active state sent from the smartphone. Next, the sleepiness baseline heart rate obtained by the correction section is corrected based on fatigue degree, sleep time, and state of meals. Thereafter, the corrected sleepiness baseline heart rate (correction sleepiness baseline heart rate) is sent to the smartphone. Sleepiness level calculation section of the smartphone calculates sleepiness level of the subject based on correction sleepiness baseline heart rate and heart rate obtained by I/F.

20 Claims, 10 Drawing Sheets

(51) Int. Cl.
 *G06K 9/00* (2006.01)
 *A61B 5/11* (2006.01)
 *A61B 5/024* (2006.01)
 *B60W 40/08* (2012.01)

(52) U.S. Cl.
 CPC .......... *G06K 9/00845* (2013.01); *A61B 5/024* (2013.01); *A61B 5/1103* (2013.01); *A61B 5/6893* (2013.01); *B60W 40/08* (2013.01)

(56) References Cited

U.S. PATENT DOCUMENTS

2006/0038689 A1* 2/2006 Ikegami ............. A61B 5/02416
 340/575
2008/0071177 A1 3/2008 Yanagidaira et al.
2015/0327803 A1 11/2015 Fujita et al.

FOREIGN PATENT DOCUMENTS

| JP | 2014-012042 | 1/2014 |
| JP | 2014-117425 | 6/2014 |
| WO | WO 2005/112764 | 12/2005 |

* cited by examiner

| STATE | CONTENT | LOCATION | ACCELERATION | SPEED | DEVICE |
|---|---|---|---|---|---|
| sta1 | REST | LIVING ROOM | SMALL | SMALL | WATCH |
| sta2 | DRIVING | VEHICLE | MIDDLE | LARGE | DRIVING SEAT |
| sta3 | WORKING | OFFICE | LARGE | MIDDLE | CHAIR |
| sta4 | SLEEP | BED | SMALL | SMALL | BED |

| STATE | CONTENT | a | b |
|---|---|---|---|
| sta1 | REST | 0.2 | 0.2 |
| sta2 | DRIVING | 0.5 | 0 |
| sta3 | WORKING | 0.1 | 0.2 |
| sta4 | SLEEP | 0.2 | 0.2 |

FIG. 6A
| | HEART RATE | SLEEPINESS BASELINE HEART RATE | SLEEPINESS LEVEL |
|---|---|---|---|
| 15 MINUTES BEFORE | 78 | 74 | 1 |
| 12 MINUTES BEFORE | 76 | 74 | 1 |
| 9 MINUTES BEFORE | 74 | 74 | 1 |
| 6 MINUTES BEFORE | 72 | 74 | 2 |
| 3 MINUTES BEFORE | 70 | 74 | 4 |
| CURRENT | 69 | 74 | 5 |
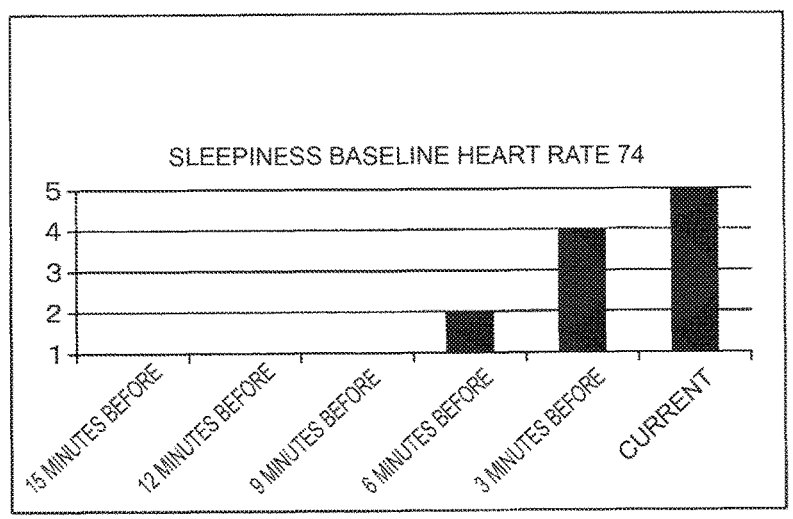
FIG. 6B
FIG. 7
| TIME | sta1 | sta2 | sta3 |
|---|---|---|---|
| t1 | 60 | 63 | 65 |
| t2 | 55 | 51 | 64 |
| t3 | 58 | 53 | 66 |
| t4 | 59 | 62 | 66 |
FIG. 8

FIG. 9A

| TIME | sta1 | sta2 | sta3 |
|------|------|------|------|
| t1 | 60 | | |
| t2 | | | 64 |
| t3 | | 53 | |
| t4 | | | 66 |

FIG. 9B

| TIME | sta1 | sta2 | sta3 |
|------|------|------|------|
| t1 | 60 | 63 | 65 |
| t2 | 55 | 51 | 64 |
| t3 | 58 | 53 | 66 |
| t4 | 59 | 62 | 66 |

FIG. 10

| FATIGUE LEVEL | CORRECTION VALUE |
|---------------|------------------|
| 4 | 10 |
| 3 | 8 |
| 2 | 4 |
| 1 | 2 |
| 0 | 0 |

FIG.11
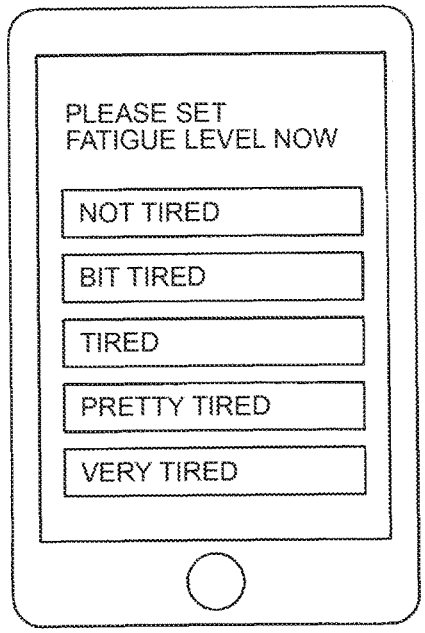
FIG.12
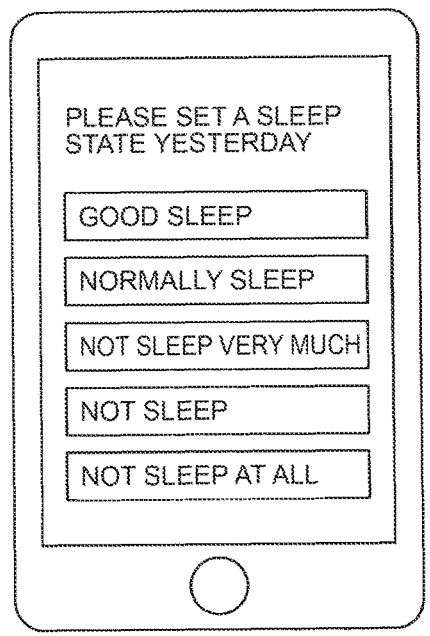
FIG.13
| | CORRECTION VALUE AFTER EATING |
|---|---|
| AFTER EATING ~ 1 HOUR AFTER | +3 |
| 1 HOUR ~ 2 HOUR AFTER | +5 |
| 2 HOUR ~ 3 HOUR AFTER | +3 |
| 3 HOUR ~ | 0 |

| | FATIGUE LEVEL | | | | | |
|---|---|---|---|---|---|---|
| | | 4 | 3 | 2 | 1 | 0 |
| SLEEP LEVEL | 4 | 10 | 9 | 7 | 6 | 5 |
| | 3 | 9 | 8 | 6 | 5 | 4 |
| | 2 | 7 | 7 | 5 | 4 | 3 |
| | 1 | 6 | 5 | 4 | 2 | 1 |
| | 0 | 5 | 4 | 3 | 1 | 0 |

|  | CORRECTION VALUE |
|---|---|
| GO BACK TO HOME | +3 |
| GO TO RESORT | -3 |

| DISTANCE | CORRECTION VALUE |
|---|---|
| 0 — 20% | -3 |
| 20% — 40% | 0 |
| 40% — 60% | +3 |
| 60% — 80% | 0 |
| 80% — 100% | -3 |

|  | CORRECTION VALUE |
|---|---|
| EXPRESSWAY | +5 |
| COUNTRY WAY | +3 |
| GENERAL ROAD | 0 |
| NARROW STREET | -3 |

SLEEPINESS CALCULATION DEVICE

The present invention relates to a sleepiness calculation device for calculating sleepiness of a subject.

BACKGROUND OF THE INVENTION

For example, in order to detect a drowsy driving in a vehicle, detecting a drowsy state from a driver's heart rate is suggested (for example, see Patent Literature 1 or 2).

In the Pattern Literature 1, an average value of RRI (R-R Interval) value detected by a heartbeat sensor during wakefulness and a predetermined multiple of an integral value of the RRI value exceeding the average value are set as a threshold value. When a value after integrating the RRI value exceeding the average value exceeds the threshold value, it is determined to be dozing.

In the patent Literature 2, a heartbeat interval data in which the RRI is arranged time-serially based on a heartbeat waveform of a subject in a rest state measured by a sensor is obtained. Then, frequency analysis of the heartbeat interval data is performed, and the frequency analysis result of heart fluctuation including power spectral density (PSD) in a frequency at a certain time and total power (TP) of autonomic nerve is obtained. Next, the frequency analysis result is set as an initial state, a sleepiness scale in which an origin of sleepiness position and an origin of a waking position are set is determined based on the estimated sleepiness position and the estimated waking position including the initial state. Then, a sleepiness of a subject is determined based on the sleepiness scale.

CITATION LIST

Patent Literature

Patent Literature 1: JP 3252586 B
Patent Literature 2: JP 2014-12042 A

SUMMARY OF THE INVENTION

Technical Problem

In the method described in the Patent Literature 1, data when wakening initially is referenced. However, the initial state differs from person to person, and the average value of RRI values cannot be set appropriately. Therefore, there is a problem that the method cannot deal with the difference of initial state by a person.

Further, in the method described in the Patent Literature 2, there is the following problem. The responses to heartbeat information and sleepiness scale are changed in various factors. Even based on a resting state, there are various changes such as a change by day or certain time. For example, it is known that time in which sleepiness becomes strong is early 3 to 4 o'clock in the early morning, and is 3 to 4 o'clock during the day. Therefore, it is difficult to accurately estimate sleepiness with only heartbeat information. Further, driving is a kind of stress loading condition, and baseline of a heart rate is different on a road state (urban area or expressway). Further, an initial state of measurement start is not constant. For this reason, measurement could not be performed according to changes such as a case that a subject is sleepy from the beginning, or the subject is not sleepy initially.

Furthermore, it is necessary to set heart rate and so on which serves as a baseline like the Patent Literatures 1 and 2 so as to determine sleepiness. However, heart rate is individual for every person, and varies according to time or active state. Moreover, sleepiness is dependent on past actions (activity) such as a sleep state (whether a subject slept well in a previous day or not), a meal state (whether a subject took meal or not), or a fatigue state (whether a subject is tired or not).

The methods described in the Patent Literatures 1 and 2 do not take into account actions of the subject. Therefore, a sleepiness detection may not be accurately performed depending on the action of the subject.

In view of the above problem, the present invention aims to provide a sleepiness calculation device which can calculate sleepiness with a high degree of accuracy in view of current action of the subject and past action thereof.

In order to solve the object, the present invention is a sleepiness calculation device including: a biological information acquisition section for obtaining biological information on heartbeat of a subject; an active state acquisition section for obtaining a current active state of the subject; a sleepiness baseline heart rate acquisition section for obtaining a sleepiness baseline heart rate as a first baseline heart rate according to the current active state from a sleepiness baseline heart rate storage section storing the sleepiness baseline heart rate of the subject for each active state; and a sleepiness level calculation section for calculating information on sleepiness of the subject based on the first baseline heart rate and the biological information.

Further, the present invention is an information processing device including an active state acquisition section for obtaining an active state of a subject; an active history acquisition section for obtaining information on a past active state of the subject; a sleepiness baseline heart rate acquisition section for obtaining a sleepiness baseline heart rate of the subject as a first baseline heart rate according to the active state from a sleepiness baseline heart rate storage section for storing the sleepiness baseline heart rate of the subject for each active state; and a correction section for correcting the first sleepiness baseline heart rate based on the information on the past active state obtained by the active history acquisition section.

Further, the present invention is a sleepiness calculation method executed in a sleepiness calculation device for calculating sleepiness of a subject comprising: a biological information acquisition step of obtaining biological information on heartbeat of a subject; an active state acquisition step of obtaining a current active state of the subject; a sleepiness baseline heart rate acquisition step of obtaining a sleepiness baseline heart rate as a first baseline heart rate according to the current active state from a sleepiness baseline heart rate storage section storing the sleepiness baseline heart rate of the subject for each active state and a sleepiness level calculation step of calculating information on sleepiness of the subject based on the first baseline heart rate and the biological information.

Further, the present invention is a sleepiness calculation program allowing a computer to execute the sleepiness calculation method described above.

Further, the present invention is a storage medium readable by a computer storing the sleepiness calculation program described above.

BRIEF DESCRIPTION OF THE DRAWINGS

FIGS. 6A and 6B are explanatory diagrams of a display example of a sleepiness display section shown in FIG. 2;

FIG. 7 is a table showing an example of a sleepiness standard heart rate table shown in FIG. 3;

FIG. 8 is another configuration example for calculating and setting the sleepiness standard heart rate table;

FIGS. 9A and 9B are explanatory diagrams of interpolation of the sleepiness standard heart rate table;

FIG. 10 is a table of correction values corresponding to fatigue levels;

FIG. 11 is an example of a screen in which subject inputs a fatigue degree;

FIG. 12 is an example of a screen in which subject inputs a sleep state;

FIG. 13 is a table of correction values corresponding to elapsed time after eating;

DESCRIPTION OF THE PREFERRED EMBODIMENT

Figure 1:
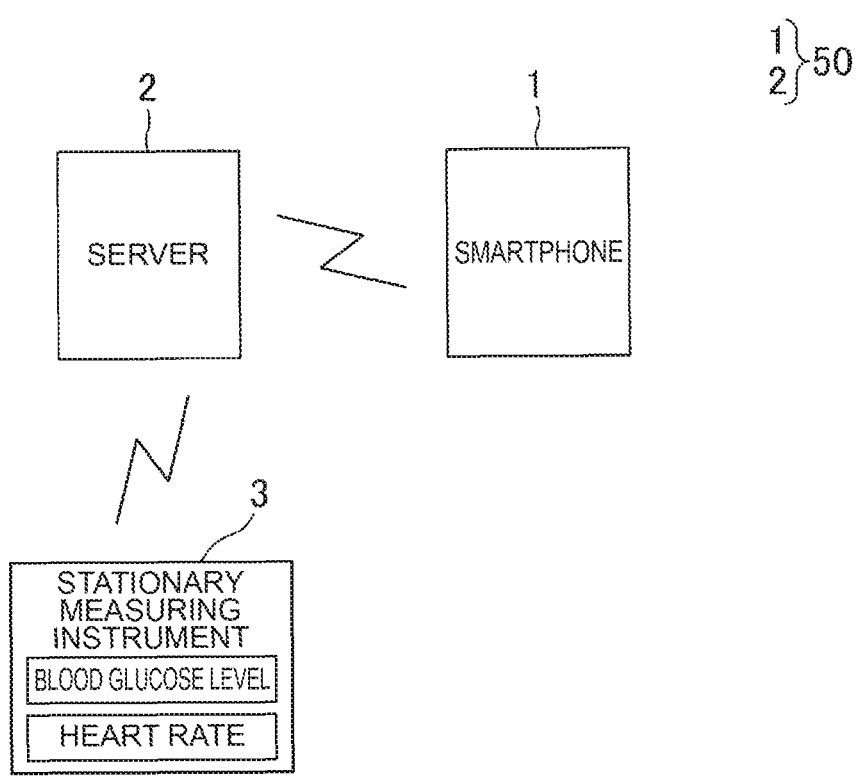
FIG. 1 is a schematic configuration diagram of a sleepiness calculation device according to a first embodiment in the present invention.

Hereafter, a sleepiness calculation device according to one embodiment of the present invention will be explained. The sleepiness calculation device in the embodiment of the present invention obtains a biological information on a heart rate of a subject in a biological information acquisition section, obtains a current active state which is a current active state of the subject in an active state acquisition section, and obtains information on a past active state of the subject in an active history acquisition section. Next, a sleepiness baseline heart rate is obtained from a sleepiness baseline heart rate storage section in which the sleepiness baseline heart rate of the subject is stored for every the active state depending on the active state which is obtained by the active state acquisition section in the sleepiness baseline heart rate acquisition section. Then, the sleepiness baseline heart rate which is obtained by the sleepiness baseline heart rate acquisition section in a correction section is corrected based on information on the past active state which is obtained by the active history acquisition section. Further, a sleepiness level calculation section calculates information on the sleepiness of the subject based on the sleepiness baseline heart rate, which is corrected by the correction section, and the biological information, which is obtained by the biological information acquisition section. By doing that, the sleepiness baseline heart rate can be corrected based on the past active state of the subject. Therefore, sleepiness calculation can be performed with a high degree of accuracy in view of not only current actions but also past actions.

Further, the active history acquisition section may obtain at least one of past sleep information of the subject, past meal information, and fatigue information associated with the past action. By doing so, the sleepiness baseline heart rate can be corrected in consideration of the past sleep information of the subject, the past meal information, and the fatigue information associated with the paste action. Thus, the sleepiness level including those factors can be calculated.

Further, the active history acquisition section may obtain a past stay history at a specific point the subject. By doing so, the past action can be estimated based on the specific portion such as a restaurant or a hot spring where the subject stayed in the past, and the sleepiness baseline heart rate can be corrected.

Furthermore, an active prediction section for predicting an action of the subject may also be provided. The correction section may further correct the sleepiness baseline heart rate obtained by the sleepiness baselines heart rate acquisition section based on the action predicted by the active prediction section. By doing so, in addition to the past action, the sleepiness baseline heart rate can be corrected in consideration of future plans, for example schedule for going to play.

Moreover, a destination information acquisition section for obtaining information on a destination of the subject may be further provided. The active prediction section may predict an action of the subject based on information on the destination. By doing so, future plans like that the destination itself is home or travel can be predicted.

In addition, a current location information acquisition section for obtaining information on a current location of the subject may be provided. The correction section may correct the sleepiness baseline heart rate which is obtained by the sleepiness baseline heart rate acquisition section based on information on the current location which is obtained by the current location information acquisition section when the current active state, which is obtained by the active state acquisition section, is driving a vehicle. By doing so, when the subject is driving a vehicle, the sleepiness baseline heart rate can be corrected according to a situation of a currently traveling road.

Further, the biological information acquisition section may obtain measurement time of the obtained biological information, and the sleepiness baseline heart rate acquisition section may obtain the sleepiness baseline heart rate from the sleepiness baseline heart rate storage section in which the sleepiness bassline heart rate of the subject is stored for every time and the active state according to the measurement time and the active state. By doing so, the sleepiness baseline heart rate can be selected in consideration of time in addition to the active state. Therefore, sleepiness can be calculated more accurately.

Further, the sleepiness level calculation section may calculate information on the sleepiness of the subject based on a sleepiness prediction parameter preset for each active state.

By doing so, a plurality of elements included in the biological information on heart rate can be weighted according to the active state.

Further, the sleepiness calculation device has a display section for displaying information on the sleepiness to the subject and an input section in which assessment of the subject to information on the sleepiness displayed on the display section is inputted. Furthermore, the sleepiness lever calculation section may update the sleepiness baseline heart rate stored in the sleepiness baseline heart rate storage section based on the assessment inputted by the input section, and calculate information on the sleepiness. By doing so, the subject can subjectively evaluates information on the sleepiness calculated by the sleepiness level calculation section. Further, the result of the subjective evaluation is fed back, and the sleepiness level calculation section can again calculate information on the sleepiness. Therefore, information on sleepiness can be calculated more accurately according to the individual's feeling.

Further, an information processing device according to one embodiment in the present invention obtains an active state of a subject in an active state acquisition section, and obtains information on a past active state of the subject in an active history acquisition section. Furthermore, a correction section corrects the sleepiness baseline heart rate based on the information on the past active state obtained by the active history acquisition section. The sleepiness baseline heart rate is selected from the sleepiness baseline heart rate storage section according to the active state obtained by the active state acquisition section. By doing so, the sleepiness baseline heart rate can be corrected based on the past active state of the subject.

Further, a sleepiness calculation device according to another embodiment of the present invention obtains obtaining biological information on heartbeat of a subject in a biological information acquisition section, and obtains a current active state of the subject in an active state acquisition section. Next, an active prediction section predicts active state of the subject. Next, a sleepiness baseline heart rate acquisition section obtains a sleepiness baseline heart rate from a sleepiness baseline heart rate storage section storing the sleepiness baseline heart rate of the subject for each active state. Next, a correction section corrects the sleepiness baseline heart rate obtained by the sleepiness baseline heart rate acquisition section based on the active state predicted by the active prediction section, and a sleepiness level calculation section calculates information on sleepiness of the subject based on the sleepiness baseline heart rate corrected by the correction section and the biological information obtained by the biological information acquisition section. By doing so, the sleepiness baseline heart rate can be corrected in consideration of future schedule of the subject. Therefore, sleepiness calculation can be performed with a high accuracy in view of not only the current actions but also future actions.

Further, in a sleepiness calculation method according to one embodiment of the present invention, a biological information acquisition step obtains biological information on heartbeat of a subject, an active state acquisition step obtains a current active state of the subject, and an active history acquisition step obtains information on a past active state of the subject. Further, a sleepiness baseline heart rate acquisition step obtains a sleepiness baseline heart rate from a sleepiness baseline heart rate storage section storing the sleepiness baseline heart rate of the subject for each active state according to the current active state. Next, a correction step corrects the sleepiness baseline heart rate obtained by the sleepiness baseline heart rate acquisition section based on the information on the past active state obtained by the active history acquisition section. Further, a sleepiness level calculation step calculates information on sleepiness of the subject based on the sleepiness baseline heart rate corrected by the correction section and the biological information obtained by the biological information acquisition section. By doing that, the sleepiness baseline heart rate can be corrected based on the past active state of the subject. Therefore, the sleepiness calculation can be performed with a high accuracy in view of not only the current actions but also past actions.

Further, the above sleepiness calculation method may be a sleepiness calculation program executed by a computer. By doing that, the sleepiness baseline heart rate can be corrected based on the past active state of the subject by using the computer. Therefore, the sleepiness calculation can be performed with a high accuracy in view of not only the current actions but also past actions.

Further, the above sleepiness calculation program may be stored in a storage medium readable by a computer. By doing that, the sleepiness calculation program can be provided with and without mounting it into a device, and version upgrading or the like of the program can be easily executed.

Example 1

A sleepiness calculation device according to a first embodiment of the present invention will be explained with reference to FIGS. 1 to 3. As shown in FIG. 1, the sleepiness calculation device 50 according to the embodiment of the present invention has a smartphone 1, and a server 2 as an information processor. Further, the server 2 is able to communicate with a stationary measuring instrument 3. The stationary measuring instrument 3 is located for example inside a building, and is able to measure heart rate of a subject and blood glucose level. When the above measurement is performed, the stationary measuring instrument 3 displays a measured result to the subject, and sends it to the server 2. The server 2 stores the measured result of the stationary measuring instrument 3.

Figure 2:
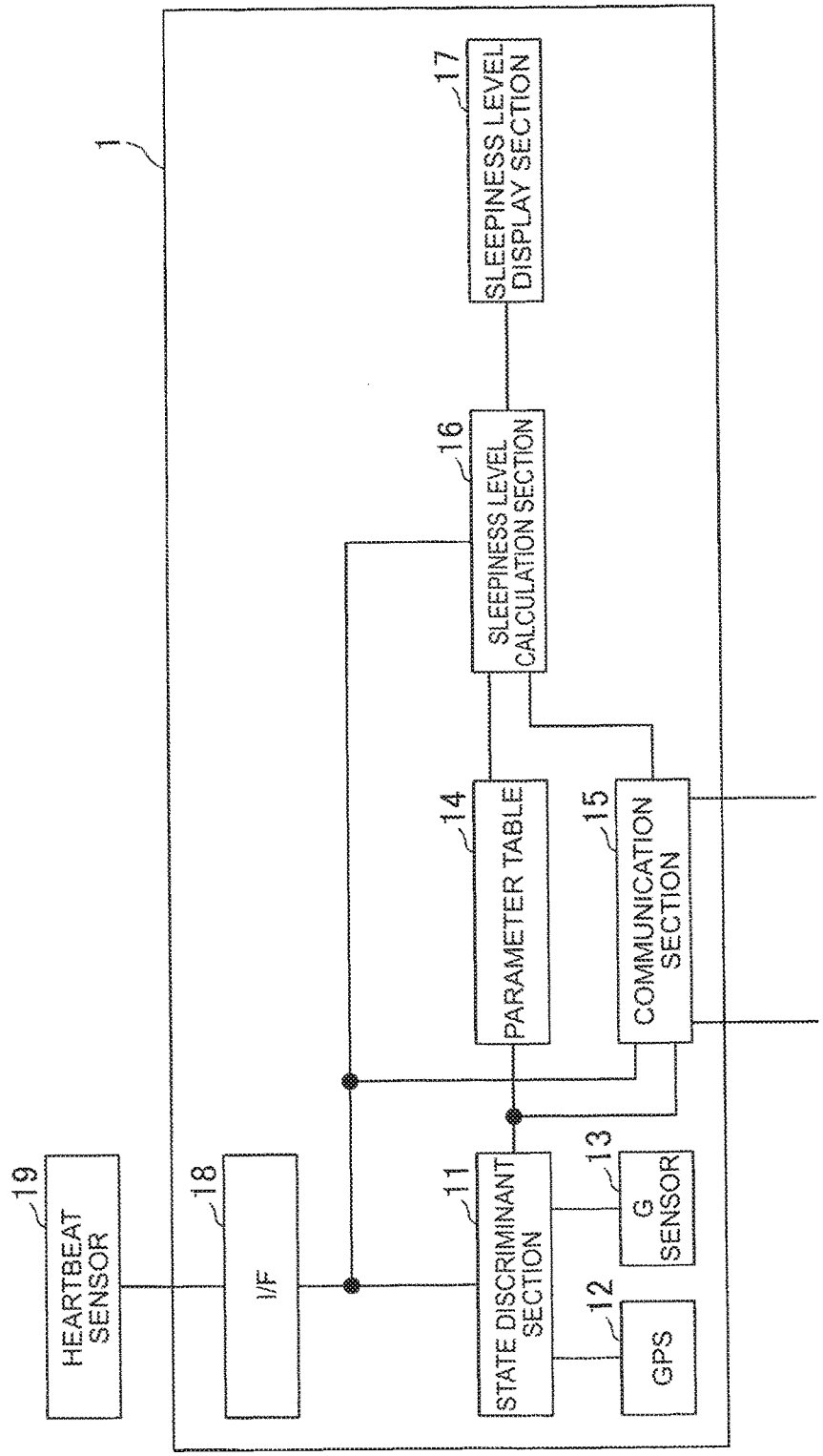
FIG. 2 is a schematic configuration diagram of a smartphone shown in FIG. 1.

As shown in FIG. 2, the smartphone 1 has a state discriminant section 11 as an active state acquisition section, a GPS receiver 12, a G sensor 13, a parameter table 14, a communication section 15, a sleepiness level calculation section 16, a sleepiness level display section 17 as a display section, and a I/F 18 as a biological information acquisition section. Further, in the smartphone 1, a heartbeat sensor 19 is connected.

The structure of the smartphone 1 shown in FIG. 2 may be configured as, for example, an application program (APP). Further, the smartphone 1 may have the heartbeat sensor 19.

Also, in the embodiment of the present invention, the smartphone 1 is explained, but the present invention is not limited to the smartphone 1. For example, the present invention may be applied to a mobile phone, a tablet device, a wristwatch device or the like. Alternatively, the present invention may be applied to on-vehicle equipment such as a car navigation system.

The heartbeat sensor 19 can use a well-known sensor which can obtain at least heart rate as biological information on heartbeat. For example, various sensors like a wristwatch type sensor can be used. Further, the heartbeat sensor 19 is not limited to one type. A plurality of types heartbeat sensor may be used depending on an active state described below.

In the smartphone 1 having the above structure, an arithmetic device such as a CPU functions as the state discriminant section 11 and the sleepiness level calculation section 16. Further, a memory medium such as a flash memory functions as the parameter table 14. Further, a display device such as a liquid crystal display functions as the sleepiness level display section 17. A communication control section communicating to the heartbeat sensor 19 functions as I/F 18. Furthermore, the GPS receiver 12 and the G sensor 13 can use a thing which is built into the smartphone 1.

The state discriminant section 11 determines a present active state (current active state) of the subject such as a rest state, a driving state, a working state, a sleeping state, and so on based on current location information and acceleration information (current location and acceleration where the subject is located) of the smartphone 1 inputted from the GPS receiver 12 or the G sensor 13. That is, the state discriminant section 11 obtains the current active state of the subject.

The GPS receiver 12 receives electric waves emitted from a plurality of GPS (Global Positioning system) statellites as is commonly known, obtains the current location information (latitude and longitude), and outputs it to the state discriminant section 11.

The G sensor 13 is a so-called acceleration sensor. For example, if the G sensor 13 is 3-axis accelerometer, it is possible to measure acceleration in three directions of XYZ axis. The G sensor 13 outputs the measured acceleration to the state discriminant section 11.

Figures 3, 4, 5:
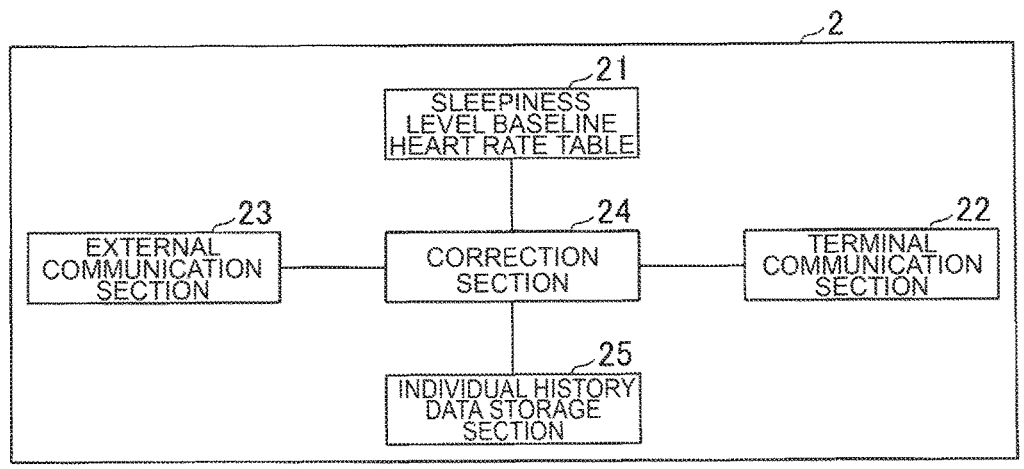
FIG. 3 is a schematic configuration of a server shown in FIG. 1.
FIG. 4 is a table showing a discriminant example of an active state in state discriminant section shown in FIG. 2.
FIG. 5 is a table showing an example of a parameter table shown in FIG. 2.

A discriminant example of the active state in the state discriminant section 11 is shown in FIG. 4. FIG. 4 is an example of a table so as to determine the active state. In the table of FIG. 4, the active states are shown. A content of a state sta 1 is rest state, a content of a state sta 2 is a driving state, a content of a state sta 3 is a working state, and a content of a state sta 4 is a sleep state. Of course, the active states may include contents other than contents shown such as exercise, hard work and the like.

In the table of FIG. 4, when location information is a living room, acceleration information is small, speed is small, and the device is a watch, it is determined as the state sta 1 (rest). Herein, speed may be calculated, for example, from a change of the current location information. A device indicates a type of the heartbeat sensor 19 or a location in which the heartbeat sensor 19 is installed. The type of the heartbeat sensor 19 and the location may be obtained from the heartbeat sensor 19, and may be set by the subject.

Further, when the current location information is a vehicle, acceleration information is large, speed is large, and the device is a driving seat, it is determined as the state sta 2 (driving). When the current location information is an office, acceleration information is large, speed is medium, and the device is a chair, it is determined as the state sta 3 (working). Further, when the current location information is a bed, acceleration information is small, speed is small, and the device is a bed, it is determined as the state sta 4 (sleep). Furthermore, specially, acceleration information and speed are a small example. Thus, specific numerical values and the like can arbitrarily be changed on setting as appropriate.

Also, in the table of FIG. 4, the active state is determined based on the current location information, acceleration information, speed information, and device information, however it may be determined based on any only one of contents, or only two contents or three contents. Further, the active state may be determined based on heart rate measured by the heartbeat sensor 19. For example, a rough determination can be performed. More specifically, when a heart rate change is small, it can be determined that the active state is the rest state or the sleep state. When a heart rate is low but it varies, it can be determined that the active state is the driving state or the working state.

The parameter table 14 has a table in which a sleepiness prediction parameter described below is set for each active state. Then, based on the result determined by the state discriminant section 11, the sleepiness prediction parameter corresponding to the active state is outputted to the sleepiness level calculation section 16. An example of the table is shown in FIG. 5.

As shown in FIG. 5, two types, a, b are set to the sleepiness prediction parameter. In an example of FIG. 5, when a state is the sta 1 (rest), the sleepiness prediction parameter a is 0.2, and the sleepiness prediction parameter b is 0.2. When a state is the sta 2 (driving), the sleepiness prediction parameter a is 0.5, and the sleepiness prediction parameter b is 0. Further, when a state is the sta 3 (working), the sleepiness prediction parameter a is 0.1, and the sleepiness prediction parameter b is 0.2. When a state is the sta 4 (sleep), the sleepiness prediction parameter a is 0.2, and the sleepiness prediction parameter b is 0.2. As is clear from the table in FIG. 5, in the sleepiness prediction parameters a and b, a value in range of 0-1 is set.

The communication section 15 communicates with the server 2. The communication section 15 sends the heart rate (heart fluctuation may be included) measured by the heartbeat sensor 19, measurement time, and the active state determined by the state discriminant section 11 to the server 2. The communication section 15 receives correction sleepiness baseline heart rate sent from the server 2. The correction sleepiness baseline heart rate is sleepiness baseline heart rate corrected with the following method. The sleepiness baseline heart rate will be described later.

The sleepiness level calculation section 16 calculates a sleepiness level (information on sleepiness) based on the heart rate measured by the heartbeat sensor 19, the sleepiness prediction parameter outputted from the parameter table 14, and the correct sleepiness baseline heart rate in which the communication section 15 is received from the server 2.

The sleepiness level is a difference between current heart rate and the sleepiness baseline heart rate when the current heart rate is lower than the sleepiness baseline heart rate, and is calculated such that sleepiness feels strongly according to a rate that the current heart rate decreases than the sleepiness baseline heart rate.

Herein, precondition for calculating the sleepiness level will be explained. In order to estimate a balance of autonomic nerve from the heartbeat fluctuation, high-frequency fluctuation component (HF component) corresponding to breathing variation and low-frequency component corresponding to Mayer wave which is blood pressure variation are extracted from time-series data about the heartbeat fluctuation, and both sizes are compared. HF component reflecting breathing variation appears to heartbeat fluctuation only when parasympathetic nerve is tense (activated). On the other hand, LF component appears to heartbeat fluctuation when sympathetic nerve is tense and when parasympathetic nerve is also tense.

HF component commonly uses the square root of a value obtained by summing the intensities of HF component region (from 0.15 Hz to 0.40 Hz) of the power spectrum. HF component (HFS) differ substantially between individuals, normalization for each individual is performed, and thereby HF component is converted from 1 to 5.

$$HFS = \beta \times \sqrt{(HF)} \quad (1)$$

Herein, a value of β is determined such that an average value of HFS is 2. When the value of HFS is smaller than 1, it is set to 1, and when the value of HFS is larger than 5, it is set to 5. As a result, HFS becomes the value from 1 to 5.

In the sleepiness level calculation section 16, the sleepiness prediction parameter is a and b, R-R interval obtained from the current heart rate HR is PR, baseline R-R interval obtained from the baseline heart rate HR_ref is RR_ref, and heartbeat fluctuation is HF. The sleepiness level D is calculated by the following formula (2).

$$D = a \times (RR - RR\_ref) + b \times HFS \quad (2)$$

Herein, heart rate HR is a number of heart rate per 1 minute. Thus, R-R interval is calculated by the following formula (3).

$$RR = 60000/HR \text{ (milliseconds)} \quad (3)$$

In the same manner, RR_ref is calculated by the following formula (4).

$$RR\_ref = 60000/HR\_ref \text{ (milliseconds)} \quad (4)$$

In the embodiment of the present invention, HFS is obtained from heart rate in the sleepiness level calculation section 16, however it may be obtained from the heartbeat sensor 19. In this case, the biological information obtained by I/F 18 becomes a high frequency component of heart rate and heartbeat fluctuation.

Herein, setting the sleepiness prediction parameters a and b respectively will be explained. For example, sleepiness during driving is likely to occur in monotonous driving (highway etc.), and functional deterioration accompanied by sleepiness is caused. In such functional deterioration, heart rate, blood pressure and so on is calmed in physiological function, and abnormalities of eye movements and brain wave appears. In subjective symptom, a feeling of fatigue is increased centering on sleepiness, lassitude or fatigue of limbs, and loss of concentration feels strongly. In capacity to act, response time is extended and varied greatly, accuracy is decreased, and it also leads to dangerous condition due to closed eyes or slumber.

The state of sleepiness is categorized as follows according to a function of automatic nerve.

<1. A Case that there is No Sleepiness>

The above case is a state that sympathetic nerve is increased, and parasympathetic nerve is suppressed. Heart rate HR is large, and the high frequency component HF of heartbeat fluctuation is small.

<2. A Case that there is a Sign of Sleepiness>

Due to a monotonous driving or fatigue, although there is little awareness of sleepiness psychologically, the sign of sleepiness appears physiologically. Since an action of sympathetic nerve is changed from the increased state to inhibitory state, heart rate is decreased.

<3. A Case that Sleepiness Occurs>

Sympathetic nerve is kept to be suppressed, but an action of parasympathetic nerve is changed to the increased state. Therefore, heart rate HR is decreased, and the high frequency component of heartbeat fluctuation is increased.

<4. A Conflict State Against the Sleepiness>

The subject feels danger, and a tension state occurs in order to resist sleepiness. When the subject is surprised, the cation of sympathetic nerve is intermittently increased, and the high frequency component HF of heartbeat fluctuation is decreased.

<5. A State that Cannot Resist Sleepiness>

Tension is lost, and dozing is begun. Since the action of sympathetic nerve is suppressed, heart rate HR is decreased.

In the above classification, during normally drowsy driving the subject changes from the 1 state (the case that there is no sleepiness) to the 2 state (the case that there is a sign of sleepiness), and then reaches the 4 state (the conflict state against the sleepiness) in many cases. On the other hand, in a resting state, the subject becomes from the 1 state to the 2 state, and becomes the 3 state (the case that sleepiness occurs). Thereafter, when the subject falls asleep, one reaches the 5 state (the state that cannot resist sleepiness).

Therefore, in the (2) formula, as shown in FIG. 4, during driving, the sleepiness prediction parameter b of heartbeat fluctuation is set to 0 and calculated. That is, in a driving state, the sleepiness prediction parameter a of heart rate changes is increased, and the sleepiness prediction parameter b of heartbeat fluctuation is decreased. On the other hand, in the resting state, the sleepiness prediction parameter a of heart rate changes is decreased, and the sleepiness prediction parameter b of heartbeat fluctuation is increased.

In other words, the sleepiness prediction parameters a and b are coefficients for weighting to the R-R interval and heartbeat fluctuation, respectively. In the R-R interval and heartbeat fluctuation as described above, contribution to sleepiness differs depending on active states. For this reason, by weighting to each of the R-R interval and heartbeat fluctuation, accuracy of sleepiness degree is improved.

Further, the sleepiness level calculated by the (2) formula is a range of numerical number of 1 to 5. When the sleepiness level is 1, sleepiness is small. When the sleepiness level is 5, sleepiness is large. Further, the sleepiness level D is difference between the current heart rate and the sleepiness baseline heart rate when the current heart rate is lower than the sleepiness baseline heart rate. Therefore, when a case is RR<RR_ref (HR>HR_ref), the sleepiness level is 1.

That is, since the sleepiness prediction parameter is changed depending on the active state, the sleepiness level calculation section 16 calculates the sleepiness level based on the heart rate (biological information), the active state, and the sleepiness baseline heart rate.

The sleepiness level display section 17 displays the sleepiness level calculated by the sleepiness level calculation section 16. The sleepiness level may simply display only a numerical value at that time, or may display it with bar graph or a line graph or the like such that changes in the time series can be seen.

A display example of the sleepiness level display section 17 is shown in FIGS. 6A and 6B. FIG. 6A is a table showing heart rate for each time, the sleepiness baseline heart rate and the calculated sleepiness level. FIG. 6B is a bar graph of FIG. 6A. That is, as shown in FIG. 6A, when heart rate is measured, the bar graph as shown in FIG. 6B is displayed to the subject.

The I/F 18 is an interface (I/F) to which the heartbeat sensor 19 is connected. The I/F 18 becomes an interface corresponding to a wire-line connection when the heartbeat sensor 19 is connected by a wire. Further, the I/F 18 becomes an interface corresponding to a wireless connection when the heartbeat sensor 19 is connected by radio. That is, the I/F 18 obtains biological information (heart rate, the measured time and so on) on heart rate of the subject measured.

As shown in FIG. 3, the server 2 has a sleepiness baseline heart rate table 21 as a sleepiness baseline heart rate storage section, a terminal communication section 22, an external communication section 23, a correction section 24, and an individual history data storage section.

As is commonly known, the server 2 is installed on a business facility, and is able to communicate with terminals such as a plurality of smartphones 1 via a network like an internet. Further, as described above, the server 2 is also able to communicate with the stationary measuring instrument 3. In the server 2 having the above structure, a memory such as a hard disk functions as the sleepiness baseline heart rate table 21 and the individual history data storage section 25. Furthermore, a board for controlling the network, a semiconductor circuit, and the like function as the terminal communication section 22 and the external communication section 23. Moreover, a computing device such as a CPU functions as the correction section 24.

The sleepiness baseline heart rate table 21 has a table in which the sleepiness baseline heart rate of the subject is stored for each time and for each active state. Thereafter, the sleepiness baseline heart rate table 21 outputs the sleepiness baseline heart rate corresponding to the active state to the correction section 24 based on the determination result of the active state acquisition section 11 received from the smartphone 1. An example of the table is shown in FIG. 7.

Herein, the sleepiness level baseline heart rate is heart rate when sleepiness occurs. That is, a person feels drowsy when it is equal or less than this heart rate. As a calculating method of the sleepiness baseline heart rate, for example, the sleepiness baseline heart rate is calculated by obtaining the minimum heart rate and standard deviation in an active state such as a driving state, and adding the minimum heart rate to the standard deviation.

In a case of an example in FIG. 7, sleepiness baseline heart rate is set for each state sta 1 to sta 3 in one hour interval of time t1 to t4. The time t1 to t4 indicates time such as 0 PM or 1 PM.

The sleepiness level baseline heart rate is calculated based on the standard deviation calculated based on information such as a heart rate obtained from the heartbeat sensor 19. For example, in a case of calculating baseline heart rate at 0 PM, the sleepiness baseline heart rate is calculated by obtaining heart rate of a predetermined period near 0 PM, calculating the minimum heart rate and the standard deviation, and adding the standard deviation to the minimum heart rate. Further, the active state at this time is obtained from the state discriminant section 11 of the smartphone 1, and it is set to the table as the sleepiness baseline heart rate at 0 PM in the active state.

Further, the sleepiness level baseline heart rate may be calculated and set by the smartphone 1 shown in FIG. 1. Moreover, information such as heart rate may be sent to the server 2 and then the sleepiness level baseline heart rate may be calculated by the server 2. Alternatively, it may be separately calculated and set with a configuration as shown in FIG. 8 and transferred to the sleepiness baseline heart rate table 21 of the server 2. An initial calibration section 31 calculates sleepiness baseline heart rate by the above described method.

Further, sine a person performs various actions, it is difficult to fill all of times and active states of the sleepiness baseline heart rate table 21 even if heart rate for 24 hours is measured (FIG. 9A). Therefore, data may be interpolated such that a blank portion becomes smooth based on the data before and after the blank portion (FIG. 9B).

Further, a portion filled by the interpolation in an initial state may be updated to the calculated value when the sleepiness baseline heart rate is calculated by subsequent measurement. Furthermore, another interpolation value may be updated based on the update (addition). Thereby, it is possible to improve the accuracy of the sleepiness baseline heart rate. That is, the sleepiness baseline heart rate table 21 functions as a sleepiness baseline heart rate setting section which adds or updates the sleepiness baseline heart rate based on measurement time of the heart rate and the active state of the subject detected by the state discriminant section 11 (active state acquisition section).

The terminal communication section 22 receives the heart rate (including heartbeat fluctuation) and the measurement time from the smartphone 1, and the active state determined by the state discriminant section 11. The received heart rate, the measurement time, and the active state are used in the correction section 24, and stored in the individual history data storage section 25. Further, the terminal communication section 22 sends the correction sleepiness baseline heart rate corrected by the correction section 24 to the smartphone 1. That is, the terminal communication section 22 functions as an active state acquisition section in the server 2.

The terminal communication section 22 receives the heart rate (including heartbeat fluctuation) and the measurement time from the smartphone 1, and the active state determined by the state discriminant section 11. The received heart rate, the measurement time, and the active state are used in the correction section 24, and stored in the individual history data storage section 25. Further, the terminal communication section 22 sends the correction sleepiness baseline heart rate corrected by the correction section 24 to the smartphone 1. That is, the terminal communication section 22 functions as an active state acquisition section in the server 2.

The external communication section 23 obtains information of heart rate (including measurement time) and blood glucose level from the stationary measuring instrument 3. The obtained information of heart rate and blood glucose level is stored in the individual history data storage section 25, and accumulated. Then, information on past actions from the heart rate, the active state, and the blood glucose level which are stored in the individual history data storage section 25 is obtained based on the read sleepiness baseline heart rate. The read the sleepiness baseline heart rate is corrected based on the information on past actions. The current time may be referred from a clock function built in the server 2, or may be obtained from an external NTP (Network Time Protocol) server. That is, the correction section 24 also functions as a sleepiness baseline heart rate acquisition section or a date and time acquisition section.

Herein, a method for obtaining (calculating) information on past actions in the correction section 24 will be explained. In the embodiment of the present invention, information on the past actions so as to correct the sleepiness baseline heart rate includes fatigue degree, sleeping time, and meal situation (after meal or not).

First, fatigue degree will be explained. Fatigue degree indicates the degree of current fatigue due to past actions (fatigue information associated with past actions). The subject tends to feel sleepy as fatigue degree increases. Therefore, by correcting the sleepiness baseline heart rate based on the fatigue degree, accuracy of calculation of the sleepiness level can be improved. Fatigue degree can be calculated by the high frequency component HF of heartbeat fluctuation described above and the low frequency component LF of heartbeat fluctuation. In common with the high frequency component HF, the low frequency component LF can be obtained by analyzing the frequency of R-R interval. As shown in the (3) formula, the R-R interval is the inverse of the heart rate. Therefore, the RR interval can be calculated from the heart rate stored in the individual history data storage section 25. Fatigue degree is calculated by the following (5) formula.

$$\text{Fatigue degree } HRV = LF/HF \quad (5)$$

When the average value of fatigue degree HRV is av, it can be categorized into 5 stages as below.

In a case that HRV>av, the subject is not tired at all.
In a case that av≥HRV>0.75×av, the subject is a bit tired.
In a case that 0.75×av≥HRV>0.5×av, the subject is tired.
In a case that 0.5×av≥HRV>0.25×av, the subject is pretty tired.
In a case that 0.25×av≥HRV, the subject is very tired.

In the above classification, "the subject is not tired at all" is indicated as a level 0, "the subject is a bit tired" is indicated as a level 1, "the subject is tired" is indicated as a level 2, "the subject is pretty tired" is indicated as a level 3, and "the subject is very tired" is indicated as a level 4. The sleepiness baseline heart rate is corrected according to the fatigue level as shown in FIG. 10. In a case of an example of FIG. 10, when the fatigue level is 4, 10 is added to the read sleepiness baseline heart rate. The added value becomes the correction sleepiness baseline heart rate. The added correction value is one example. Thus, it is possible to change the correction value by setting appropriately.

Further, the fatigue degree can be calculated from the result of an activity amount meter (activity amount sensor) not shown. The activity meter detects change of acceleration due to body motion with a frequency of 0.01 G or more and 2 to 3 HZ. It is known that the average activity amount at the time of awakening is about 200 times/minutes in the measurement using such activity amount meter. Therefore, current activity amount is categorized as below.

In a case that the amount of action>400, the subject is not tired at all.
In a case that 400≥the amount of action>350, the subject is a bit tired.
In a case that 350≥the amount of action>250, the subject is tired.
In a case that 250≥the amount of action>200, the subject is pretty tired.
In a case that 200≥the amount of action, the subject is very tired.

By categorizing like that, the sleepiness baseline heart rate can be corrected by using FIG. 10. Therefore, the measurement result of the action meter can be regularly sent to the server 2, and the fatigue degree can be calculated in a method for accumulated in the individual history data storage section 25.

Alternatively, a screen of fatigue degree shown in FIG. 11 may be displayed on the smartphone 1, and current fatigue degree may be selected by the subject.

Next, sleep time will be explained. Sleep time indicates whether the subject slept well on previous night or not. That is, past sleep time is indicated. If the subject cannot sleep well, it tends to sleep after that. Therefore, by correcting the sleepiness baseline heart rate based on sleep time, it is possible to improve calculation accuracy of sleepiness level. Sleep time can be estimated from the heart rate accumulated in the individual history data storage section 25 since the heart rate is decreased during sleep. Further, its sleep time is categorized as below.

In a case that sleep time>8 hours, the subject slept well.
In a case that 8 hours≥sleep time>6 hours, the subject slept normally.
In a case that 6 hours≥sleep time>2 hours, the subject could not sleep very much.
In a case that 2 hours≥sleep time>0, the subject could not sleep.
In a case that 0=sleep time, the subject could not sleep at all.

In the above classification, as with fatigue degree, "good sleep" is indicated as a level 0, "normally sleep" is indicated as a level 1, "not sleep very much" is indicated as a level 2, "not sleep" is indicated as a level 3, and "not sleep at all" is indicated as a level 4. The sleepiness baseline heart rate is corrected according to the sleep level similar to the example of FIG. 10. Of course, the correction value may be a value different from that in the example of FIG. 10.

Furthermore, regarding sleep, a screen of sleep level shown in FIG. 12 may be displayed on the smartphone 1, and current sleep level may be selected by the subject.

Next, a state of meal will be explained. The state of meals whether the subject recently had a meal or not is indicated. In the other words, current meal information is shown. It is possible to determine whether the subject had a meal or not by detecting an increase in blood glucose level. Since the blood glucose level is accumulated in the individual history data storage section 25, the state of meals is determined from the data.

As shown in FIG. 13, the correction value is added according to the elapsed time after eating. For example, if it is within 1 hour after eating, 3 is added to the read sleepiness baseline heart rate. The correction value is one example, and it can be changed by setting appropriately.

Further, a state of meals may be determined from position information of the subject. For example, the subject stayed for a certain period of time in the vicinity (within a certain range) of a specific point such as a restaurant or the like, and the heart rate rises, it is determined that the subject has a meal. The position information of the subject is able to be determined by obtaining information of the GPS receiver 12 of the smartphone 1. That is, in this case, current position information (stay history) of the subject is further stored in the individual history data storage section 25.

A flowchart of meal determination will be explained with reference to FIG. 14. The flowchart of FIG. 14 may be performed by the correction section of the server 2. Alternatively, it may be performed by the smartphone 1 so as to send the result thereof. When the flowchart is performed by the server 2, the server 2 itself has map information and position information or obtains them from an external device. When the flowchart is performed by the smartphone 1, map information application or navigation application (navigation application) must be installed.

Figures 14, 15:
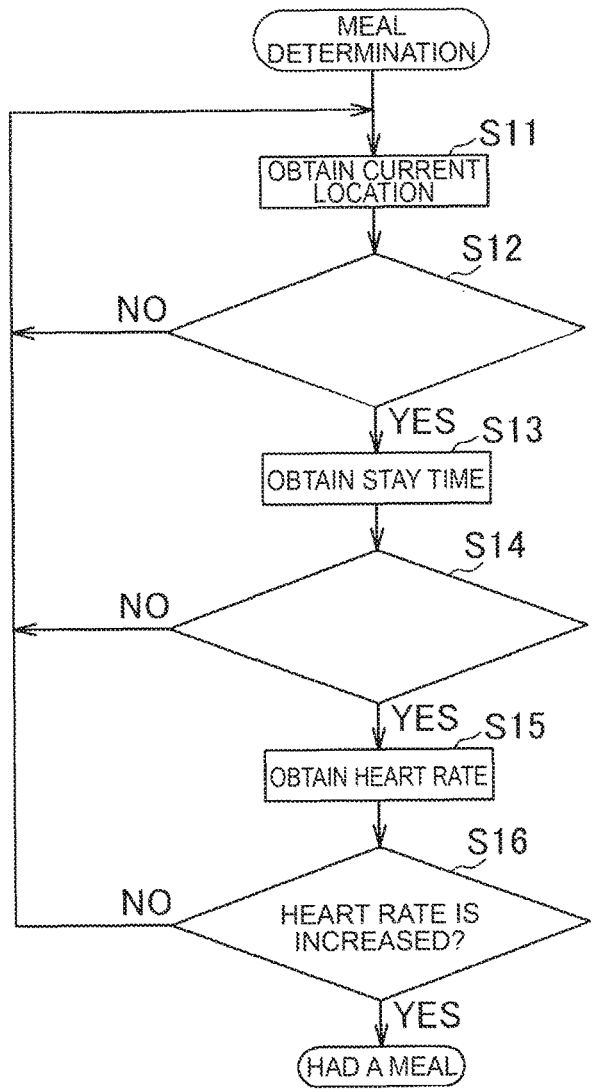
FIG. 14 is a flowchart for determining a state after eating from position information.
FIG. 15 is a table of correction values corresponding to fatigue levels and sleep levels.

First, in step S11 of FIG. 14, present location is obtained. Next, in step S12, it is determined whether there is a facility for eating a meal within a certain range or not. If there is the facility (in case of YES), visit duration is obtained in step S13. On the other hand, if there is no the facility (in case of NO), the processing returns to step S11 (it is determined that the subject is not eating).

Next, in step S14, it is determined whether the subject stays for a certain period of time or more. Thereafter, if the subject has stayed for a certain period of time or more (in case of YES), heart rate is obtained in step S15. Then, it is determined whether the heart rate rises or not in step S16. If the heart rate rises (in case of YES), it is determined that the subject had a meal. On the other hand, if the subject has not stayed for a certain period of time or more in step S14 (in case of NO), or the heart rate does not rise (in case of NO) in step S16, the processing returns to step S11 (it is determined that the subject is not eating). That is, past stay history becomes that the subject had stayed for a certain period of time or more in the facility for eating a meal (specific point).

Further, correction may be performed based on information on a plurality of past actions. For example, correction may be performed by adding a value as shown in FIG. 15 according to both states of the fatigue degree and sleep time. In case of FIG. 15, when fatigue level is 4, and sleep level is 4, 10 is added.

Furthermore, states of meals may be combined. For example, correction values of fatigue degree and sleep state in FIG. 15 is calculated, then a correction value of the state of meals is calculated, and both correction values may be added.

In the individual history data storage section 25, history data that the heart rate, the measurement time and the active state received by the terminal communication section 22, and the heart rate, the blood glucose level and the measurement time sent from the stationary measuring instrument 3 are individually stored. The server 2 may create or update the sleepiness baseline heart rate table 21 based on the history data stored in the individual history data storage section 25.

A flowchart of operation in the sleepiness calculation device 50 having the structure described above is shown in FIG. 16. First, in step S21, user ID and password allocated to each user from the smartphone 1 are sent from the communication section 15 to the server 2. In step S31, user authentication is performed in the server 2 with user ID and password sent from the smartphone 1.

Next, the active state determined by the state discriminant section 11 is sent from the communication section 15 of the smartphone 1 to the server 2. In step S32, the server 2 receives the active state sent from the smartphone 1. That is, this step functions as an active state acquisition step.

Next, in step S33, the server 2 obtains (reads) history data (such as the heart rate, blood glucose level, and the like) accumulated in the individual history data storage section 25. Then, in step S34, the active state from the sleepiness baseline heart rate table 21 the sleepiness level baseline heart rate from current time are read in the correction section 24, the read sleepiness level baseline heart rate is corrected based on the above fatigue degree, and the corrected sleepiness level baseline heart rate is sent to the smartphone 1 as a correction sleepiness baseline heart rate. That is, step S34 functions as a sleepiness baseline heart rate acquisition step, an active history acquisition step and a correction step.

Next, in step S23, the smartphone 1 receives the correction sleepiness baseline heart rate from the server 2. Then, in step S24, the sleepiness level calculation section 16 calculates sleepiness level, and displays it on the sleepiness level display section 17. That is, step S24 functions as a sleepiness level calculation step. In step S25, history data (heart rate, measurement time, etc.) is sent to the server 2. Also, history data may be sent when sending the active state in step S22.

Next, in step S35, the server 2 stores the received history in the individual history data storage section 25.

Figure 16:
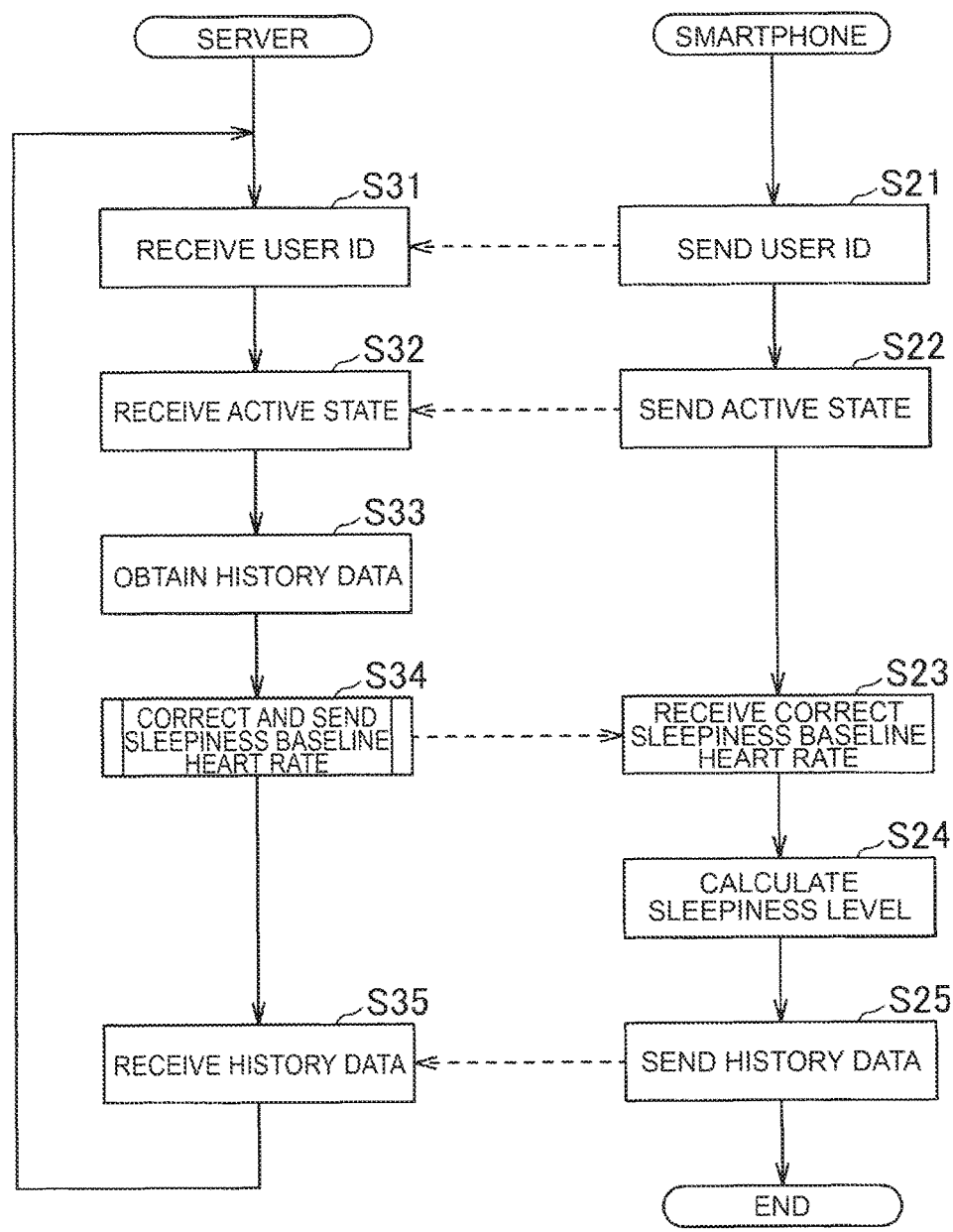
FIG. 16 is a flowchart of operation of the sleepiness calculation device shown in FIG. 1.
Figures 17, 18, 19, 20:
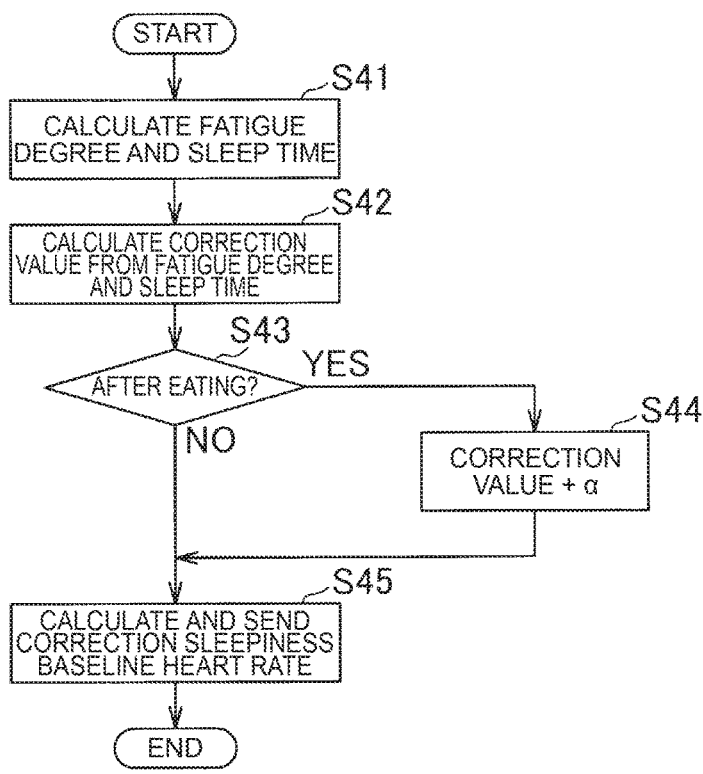
FIG. 17 is a flowchart of operation for correcting sleepiness standard heart rates shown in FIG. 16.
FIG. 18 is a table of correction values corresponding to destination of sleepiness calculation device according to a second embodiment of the present invention.
FIG. 19 is a table of correction values corresponding to the distance to the destination.
FIG. 20 is a table of correction values corresponding to the road shape.

In FIG. 17, a flowchart of operation in step S34 (correction and transmission of sleepiness baseline heart rate) of FIG. 16 is indicated. First, in step S41, fatigue degree and sleep time are calculated, and in step S42, a correction value is calculated based on the table shown in FIG. 15 from fatigue degree and sleep time.

Next, in step S43, it is judged whether the subject is after eating or not from the blood glucose level and location information as described above. In case after eating, in step S44, a correction value based on the table shown in FIG. 13 is further added to the correction value calculated (+α). In step S45, sleepiness baseline heart rate corrected by the correction value calculated in step S44 is calculated as correction sleepiness baseline heart rate, and sent. On the other hand, in case after not eating, in step S45, the sleepiness baseline heart rate corrected by the correction value calculated in step S42 is calculated as the correction sleepiness baseline heart rate, and sent.

Furthermore, in a flowchart of FIG. 17, the sleepiness baseline heart rate is corrected in each case. However, regarding to fatigue degree and sleep time, a correction value may be determined on the morning of the day, and the sleepiness baseline heart rate table may be created. In addition, the sleepiness baseline heart rate may be read based on the active state and the current time from the sleepiness baseline heart rate table created. For meal, a value of the sleepiness baseline heart rate table created may be corrected.

According to the embodiment of the present invention, in the smartphone 1, I/F 18 obtains the heart rate of the subject measured by the heartbeat sensor 19 and measurement time, determines the active state of the subject in the active state acquisition section 11, and send it to the server 2. Next, in the server 2, the sleepiness baseline heart rate is obtained from the sleepiness baseline heart rate table 21 in which the sleepiness baseline heart rate of the subject is stored in each active state according to the active state sent from the smartphone 1 in the correction section 24. Next, the sleepiness baseline heart rate obtained in the correction section 24 is corrected based on fatigue degree, sleep time and the state of meal calculated from history data which is read from the individual history data storage section 25. The corrected sleepiness baseline heart rate (correction sleepiness baseline heart rate) is sent to the smartphone 1, and sleepiness level of the subject is calculated based on the correction sleepiness baseline heart rate and the heart rate obtained by I/F 18 in the sleepiness level calculation section 16 of the smartphone 1. By doing that, the sleepiness baseline heart rate can be corrected based on the past active state of the subject. Therefore, sleepiness calculation can be performed with a high degree of accuracy in view of not only current actions but also past actions.

Further, the correction section 24 obtains information on fatigue degree, sleep time and state of meals as information on the past active state of the subject. By doing that, sleepiness baseline heart rate can be corrected in view of information on fatigue degree, sleep time and state of meals. Thus, sleepiness degree can be calculated by adding those elements.

Further, the server 2 adds or updates the sleepiness baseline heart rate stored in the sleepiness baseline heart rate table 21 based on time in which heart rate is measured and the active state of the subject determined by the active state acquisition section 11. By doing that, changes of the sleepiness baseline heart rate for each time of the active state in everyday life of the subject can be updated or added continually.

Furthermore, the sleepiness level calculation section 16 calculates sleepiness level of the subject based on a sleepiness prediction parameter predetermined for each active state. By doing that, heart rate and heartbeat fluctuation can be weighted according to the active state.

Moreover, since the sleepiness level display section 17 is provided, the subject can perceive his sleepiness specifically, and can make actions such as rest or exercise based on sleepiness level displayed.

Also, the present invention obtains three pieces of information such as fatigue degree, sleep time and state of meals in the subject, but not limited thereto. Only one of them may be used.

Further, in a case when it is judged whether the subject had a meal or not, location information is used, but it is not limited thereto. For example, after staying in a relaxation facility such as a hot spring, tension of the subject is softened. For this reason, the subject tends to be sleepy. Therefore, when the subject stays at a relaxation facility for a certain period of time or more, the sleepiness baseline heart rate may be corrected. In addition, as in the flowchart of FIG. 14, it can be judged whether the subject stayed in the relaxation facility or not. That is, past stay history becomes that the subject stayed in the relaxation facility (specific point) for a certain period of time or more.

Further, the sleepiness prediction parameter and the sleepiness baseline heart rate are selected based on the active state and measurement time in the above embodiment, however they may be selected based on only the active state. However, it is preferable to consider both the active state and measurement time because an appropriate sleepiness prediction parameter and sleepiness baseline heart rate can be selected.

Further, sleepiness level may be notified by voice in addition to the sleepiness level display section 17. Alternatively, notification by voice may be performed in case of a sleepiness level higher than a certain level.

Further, the server 2 may have both or one of the parameter table 14 and the sleepiness level calculation section 16, and the smartphone 1 may have both or one of the sleepiness baseline heart rate table 21 and the correction section 24. Furthermore, the smartphone 1 may have all of the structure without using the server 2.

Example 2

Next, the sleepiness calculation device will be explained with reference to FIGS. 18 to 20 according to a second embodiment of the present invention. Also, the same parts as those of the first embodiment described above are denoted by the same reference numerals, and explanations thereof are omitted.

In the first embodiment, the sleepiness baseline heart rate is corrected based on information on past activities, however in this embodiment future activities are predicted in addition to that, and the predicted amount is corrected. The structure is the same as the structure shown in FIGS. 1 to 3. That is, the correction section 24 functions as the active prediction section. Also, the embodiments of the present invention are explained with the smartphone 1, however may be used in a car navigation system as is apparent from the following description.

For example, when the subject comes back home by driving a vehicle such as an automobile or the like, it is anticipated that relaxing actions such as rest or sleep with relative equanimity increase from this time. For this reason, tension of the subject tends to get loose, and the subject is likely to sleep. In contrast, when the subject goes to a trip such as a resort, it is anticipated that relatively active actions such as shopping or walk increase from this time. For this reason, mood is lifted, and thereby it is considered that the subject is hard to get sleep.

Therefore, when a destination is set to a navigation app of the smartphone 1, information of the destination is sent to the server 2. Thereafter, the correction value for example shown in FIG. 18 is further added to the correction sleepiness baseline heart rate corrected in the first embodiment. Also, instead of information of the destination, information of "home" or "resort" may be sent to the server 2. That is, the terminal communication section 22 functions as the destination information acquisition section for obtaining information on the destination to which the subject move on, and the correction section 24 anticipates the action of the subject based on information on the destination.

Further, in case that the subject moves toward a resort, the subject is less likely to feel sleepiness on the subject's departure. However, in the middle point thereof, the subject is likely to get sleepy. Thus, in addition to correction of FIG. 18, correction may be performed according to a distance from the middle point to the destination as shown in FIG. 19. In the distance of FIG. 19, 0% is a departure place, and 10% is the destination. Further, the present invention is not limited to the distance. The time required from the departure point to the destination may be corrected according to the ratio of the required time from the middle point to the destination. In this case, even if the distance of FIG. 19 is changed to the required time, it can be corrected in the same way.

According to the embodiment of the preset invention, the correction section 24 anticipates action of the subject, and corrects the sleepiness baseline heart rate read from the sleepiness baseline heart rate table 21 based on the anticipated action. By doing that, in addition to past action, for example the sleepiness baseline heart rate can be corrected in consideration of future schedule such as going play from now on.

Further, the server 2 obtains information on the destination to which the subject goes from the smartphone 1 in the terminal communication section 22, and the correction section 24 anticipates action of the subject based on information on the destination. By doing that, future schedule such as whether the destination itself is home or travel can be anticipated.

Also, in the above description, correction is performed in addition to the past active state described in the first embodiment, but correction of only future prediction described in the above embodiment may be performed.

Furthermore, in case of driving a vehicle, if the current driving road is monotonous road, the subject is likely to get sleepy. Further, if it is complex roads, the subject becomes wakeful. Therefore, in addition to correction depending on the past or future prediction, as shown in FIG. 20, correction may be performed based on the shape of the current driving road.

In other words, the terminal communication section 22 obtains information on the current location in which the subject is positioned. Next, the correction section 24 corrects the sleepiness baseline heart rate obtained according to the active state based on information on the current location when the current active state of the subject obtained by the terminal communication section 22 is a case driving a vehicle. Also, driving the vehicle can be determined by the active state acquisition section 11 as described above.

Further, a route guided by a navigation app or the like may be changed based on the sleepiness level calculated by the smartphone 1. That is, a guide section for searching a route by a preset destination and guiding may be further provided. The guide section may search a route by the destination based on the sleepiness level calculated by the sleepiness level calculation section 16.

Example 3

Next, the sleepiness calculation device will be explained with reference to FIGS. 21 and 22 according to a third embodiment of the present invention. Also, the same parts as those of the first and second embodiments described above are denoted by the same reference numerals, and explanations thereof are omitted.

This embodiment is the same as the basic structure of the first embodiment (FIGS. 1 to 3). The sleepiness level shown in the first embodiment is calculated based on heart rate and so on measured by the heartbeat sensor 19, but there is a case where the calculated value and the sensation of the subject are difference. Therefore, in this embodiment of the present invention, the subject subjectively evaluates the sleepiness level displayed on the sleepiness level display section 17, and the sleepiness baseline heart rate is corrected (updated) based on the evaluation.

A specific example will be explained with reference to FIGS. 21 and 22. FIGS. 21 and 22 are display examples of the sleepiness level display section 17, illustrate changed of heart rate, a graph 171 of the sleepiness baseline heart rate, a graph 172 of the sleepiness level, and the sleepiness level. In the sleepiness level, the evaluation of the subject can be inputted by touching the displayed numerical value. That is, in the example of FIGS. 17 and 18, the sleepiness level display section 17 is a touch panel.

Figure 21:
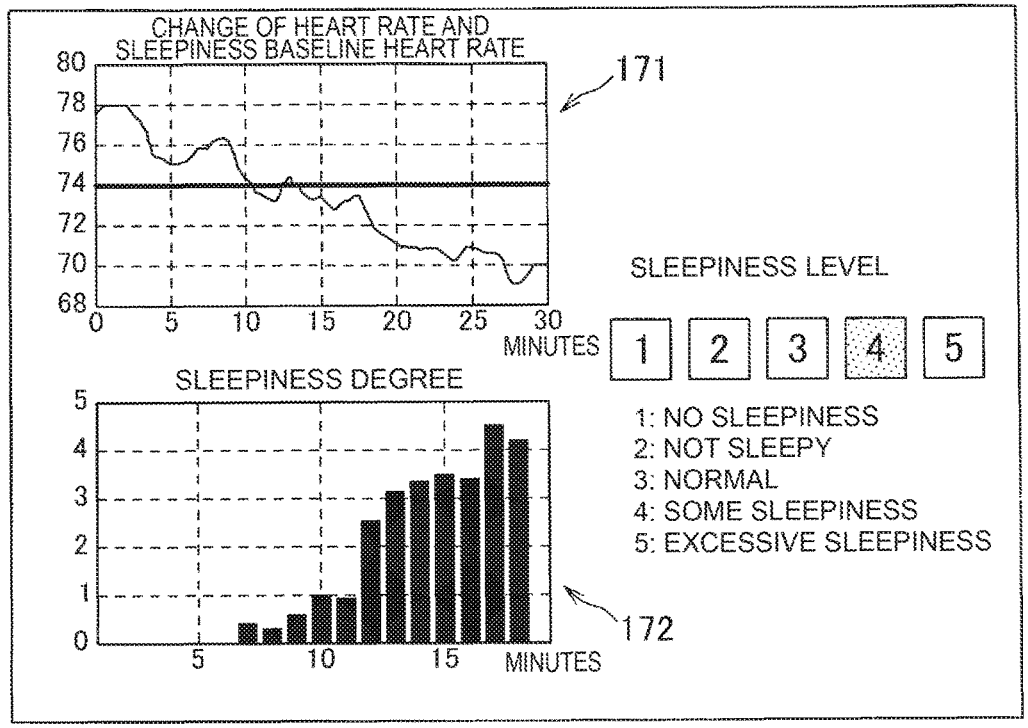
FIG. 21 is an explanatory diagram of a display example before subjective assessing a sleepiness display section of the sleepiness calculation device according to a third embodiment of the present invention.
Figure 22:
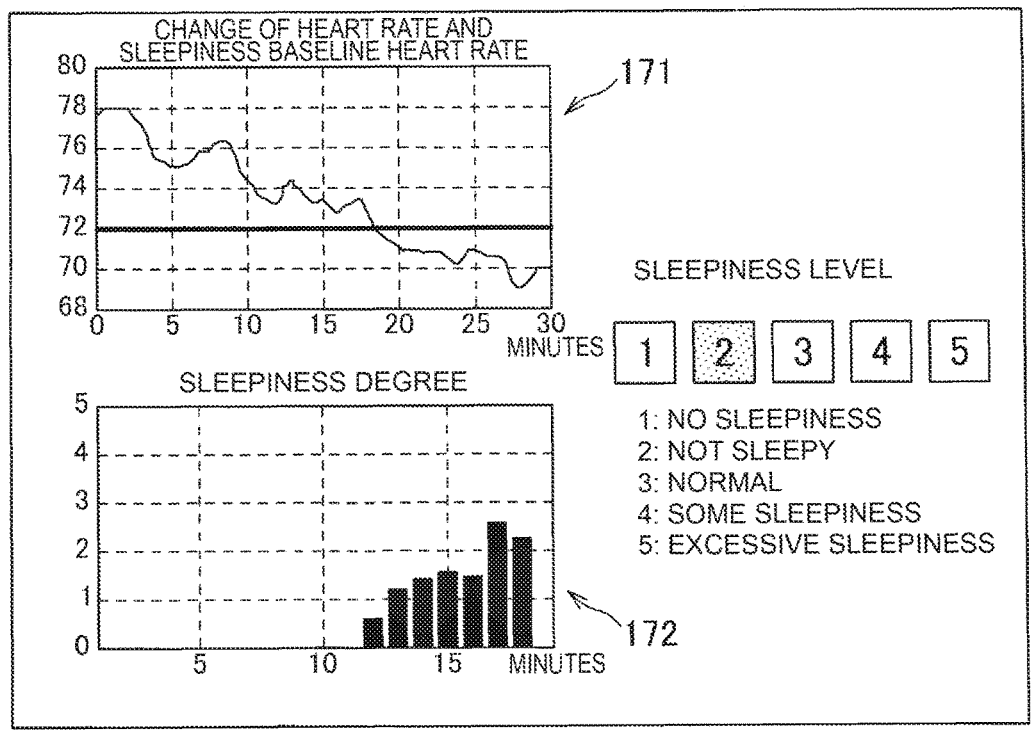
FIG. 22 is an explanatory diagram of a display example after subjective assessing a sleepiness display section of the sleepiness calculation device according to a third embodiment of the present invention.

In case of FIG. 21, the sleepiness baseline heart rate is 74. Further, current sleepiness level becomes 4 from the result calculated by the sleepiness level calculation section 16. At this time, the subject subjectively evaluates the current sleepiness level.

Based on the result of subjective evaluation, when evaluating that the sleepiness level is 2, as shown in FIG. 21, the subject selects 2 of the sleepiness level. Thereafter, the sleepiness baseline heart rate is revised according to the subjective evaluation. In case of FIG. 21, the sleepiness baseline heart rate is modified to 72. Furthermore, the sleepiness level is again calculated based on the modified sleepiness baseline heart rate, and then a graph 172 of the sleepiness level is also modified (FIG. 22).

Next, the modification of the sleepiness baseline heart rate will be explained. When the formula (2) described in the first embodiment is modified, the following formula (6) is obtained.

$$RR\_ref=RR-(D-b \times HFS)/a \quad (6)$$

Thus, by assigning the subjective evaluation to D of the above formula (6), the modified RR_ref can be calculated. Further, the sleepiness level is again calculated by the formula (2) based on the modified RR_ref. Furthermore, the RR_ref and the sleepiness baseline heart rate HR_ref are in the relation shown in the formula (4) described in the first embodiment. Therefore, the sleepiness baseline heart rate HR_ref can be easily calculated by modifying the formula (4).

The modified sleepiness baseline heart rate HR_ref is used for display of a graph 171 of changes of heart rate and the sleepiness baseline heart rate, and sent to the server 2. The modification of the sleepiness baseline heart rate in the active state and time corresponding to the sleepiness baseline heart rate table 21 is performed. Furthermore, it is not limited to the sleepiness level baseline heart rate. Various correction values may be modified. Moreover, since the correction values explained in the first and second embodiments differ in individuals, it is preferably to feed back the result of the subjective evaluation.

According to the embodiment of the present invention, a touch panel for inputting subjective evaluation of the subject for the sleepiness level illustrated in the sleepiness level display section 17 is provided. Further, the sleepiness level calculation section 16 modifies the sleepiness baseline heart rate based on the subjective evaluation inputted from the touch panel, and again calculates the sleepiness level based on the modified sleepiness baseline heart rate. By doing that, the subject can subjectively evaluates the sleepiness level calculated by the sleepiness level calculation section 16. Furthermore, the sleepiness level calculation section 16 again calculates the sleepiness level after feeding back the subjective evaluation. Thus, it is possible to more precisely calculate inform on sleepiness according to individual subjects.

The present invention is not limited to the embodiments described above. Namely, a person skilled in the art can carry out the present invention by modifying the embodiments within the subject matter of the present invention in accordance with the conventional well-known knowledge. The modification of the present invention is also encompassed by the present invention as long as the modification has the sleepiness calculation device according to the present invention.

REFERENCE SIGNS LIST 1 smartphone
2 server (information processor)
3 stationary measuring instrument
11 state discriminant section (active state acquisition section)
12 GPS receiver (current location information acquisition section)
13 G sensor
14 parameter table
15 communication section
16 sleepiness level calculation section
17 sleepiness level display section (display section, destination information acquisition section, input section)
18 I/F (biological information acquisition section)
19 heartbeat sensor
21 sleepiness baseline heart rate table (sleepiness baseline heart rate storage section)
22 terminal communication section (biological information acquisition section, active state acquisition section, current location information acquisition section, destination information acquisition section)
23 external communication section
24 correction section (sleepiness baseline heart rate acquisition section, active history acquisition section, active prediction section)
25 individual history data storage section
50 sleepiness calculation device
S35 receiving of history data (biological information acquisition step)
S32 acquiring of active state (active state acquisition step)
S33 acquiring of history data (active history acquisition step)
S34 correcting and receiving baseline heart rate (sleepiness baseline heart rate acquisition step, correction step)
S24 sleepiness level calculation (sleepiness level calculation step)

What is claimed is:
1. A sleepiness calculation device comprising:
a biological information acquisition section for obtaining biological information on heartbeat of a subject;
an active state acquisition section for obtaining a current active state of the subject;
a sleepiness baseline heart rate acquisition section for obtaining a sleepiness baseline heart rate as a first baseline heart rate according to the current active state from a sleepiness baseline heart rate storage section storing the sleepiness baseline heart rate of the subject for each active state; and a sleepiness level calculation section for calculating information on sleepiness of the subject based on the first baseline heart rate and the biological information.

2. The sleepiness calculation device according to claim 1, further comprising an active history acquisition section for obtaining information on a past active state of the subject, wherein the sleepiness level calculation section calculates information on sleepiness of the subject based on a second baseline heart rate and the biological information, the second baseline heart rate being obtained by correcting the first baseline heart rate based on information on the past active state obtained by the active history acquisition section.

3. The sleepiness calculation device according to claim 2, wherein the active history acquisition section obtains at least one of past sleep information of the subject, past meal information, and fatigue information associated with a past action.

4. The sleepiness calculation device according to claim 3, wherein the active history acquisition section obtains a past stay history of the subject on a specific point.

5. The sleepiness calculation device according to claim 3, further comprising an active prediction section for predicting an action of the subject, wherein the sleepiness level calculation section calculates information on the sleepiness of the subject based on a third baseline heart rate and the biological information, the third baseline heart rate being obtained by correcting the second baseline heart rate based on the action predicted by the active prediction section.

6. The sleepiness calculation device according to claim 2, wherein the active history acquisition section obtains a past stay history of the subject on a specific point.

7. The sleepiness calculation device according to claim 6, further comprising an active prediction section for predicting an action of the subject, wherein the sleepiness level calculation section calculates information on the sleepiness of the subject based on a third baseline heart rate and the biological information, the third baseline heart rate being obtained by correcting the second baseline heart rate based on the action predicted by the active prediction section.

8. The sleepiness calculation device according to claim 2, further comprising an active prediction section for predicting an action of the subject, wherein the sleepiness level calculation section calculates information on the sleepiness of the subject based on a third baseline heart rate and the biological information, the third baseline heart rate being obtained by correcting the second baseline heart rate based on the action predicted by the active prediction section.

9. The sleepiness calculation device according to claim 8, further comprising a destination information acquisition section for obtaining information on a destination of the subject, wherein the active prediction section predicts an action of the subject based on the information on the destination.

10. The sleepiness calculation device according to claim 8, further comprising an active prediction section for predicting an action of the subject, wherein the sleepiness level calculation section calculates information on the sleepiness of the subject based on a third baseline heart rate and the biological information, the third baseline heart rate being obtained by correcting the second baseline heart rate based on the action predicted by the active prediction section.

11. The sleepiness calculation device according to claim 9, further comprising an active prediction section for predicting an action of the subject, wherein the sleepiness level calculation section calculates information on the sleepiness of the subject based on a third baseline heart rate and the biological information, the third baseline heart rate being obtained by correcting the second baseline heart rate based on the action predicted by the active prediction section.

12. The sleepiness calculation device according to claim 1, further comprising a current location information acquisition section for obtaining information on a current location of the subject, wherein the sleepiness level calculation section calculates information on the sleepiness of the subject based on a fourth baseline heart rate and the biological information when the current active state obtained by the active state acquisition section is a state of driving a vehicle, the fourth baseline heart rate being obtained by correcting the first baseline heart rate based on information on the current location obtained by the current location information acquisition section.

13. The sleepiness calculation device according to claim 1, wherein the biological information acquisition section obtains measurement time of the obtained biological information, and the sleepiness baseline heart rate acquisition section obtains the first sleepiness baseline heart rate from the sleepiness baseline heart rate storage section in which the sleepiness baseline heart rate of the subject is stored for each time and the active state according to the measurement time and the active state.

14. The sleepiness calculation device according to claim 1, wherein sleepiness level calculation section calculates the information on sleepiness of the subject based on a preset sleepiness prediction parameter set for each active state.

15. The sleepiness calculation device according to claim 1, further comprising a display section for displaying information on the sleepiness to the subject, and an input section in which assessment of the subject to the information on the sleepiness displayed on the display section is inputted, wherein the sleepiness level calculation section updates the sleepiness baseline heart rate stored in the sleepiness baseline heart rate storage section based on the assessment inputted by the input section, and calculates the information on the sleepiness.

16. An information processing device comprising:

an active state acquisition section for obtaining an active state of a subject;

an active history acquisition section for obtaining information on a past active state of the subject;

a sleepiness baseline heart rate acquisition section for obtaining a sleepiness baseline heart rate of the subject as a first baseline heart rate according to the active state from a sleepiness baseline heart rate storage section for storing the sleepiness baseline heart rate of the subject for each active state; and a correction section for correcting the first sleepiness baseline heart rate based on the information on the past active state obtained by the active history acquisition section.

17. A sleepiness calculation device comprising:
a biological information acquisition section for obtaining biological information on heartbeat of a subject;
an active state acquisition section for obtaining a current active state of the subject;
an active prediction section for predicting an active state of the subject;
a sleepiness baseline heart rate acquisition section for obtaining a sleepiness baseline heart rate from a sleepiness baseline heart rate storage section storing the sleepiness baseline heart rate of the subject for each active state;
a correction section for correcting the sleepiness baseline heart rate obtained by the sleepiness baseline heart rate acquisition section based on the active state predicted by the active prediction section; and
a sleepiness level calculation section for calculating information on sleepiness of the subject based on the sleepiness baseline heart rate corrected by the correction section and the biological information obtained by the biological information acquisition section.

18. A sleepiness calculation method executed in a sleepiness calculation device for calculating sleepiness of a subject comprising:

a biological information acquisition step of obtaining biological information on heartbeat of a subject;
an active state acquisition step of obtaining a current active state of the subject;
a sleepiness baseline heart rate acquisition step of obtaining a sleepiness baseline heart rate as a first baseline heart rate according to the current active state from a sleepiness baseline heart rate storage section storing the sleepiness baseline heart rate of the subject for each active state;
and
a sleepiness level calculation step of calculating information on sleepiness of the subject based on the first baseline heart rate and the biological information.

19. A sleepiness calculation program allowing a computer to execute the sleepiness calculation method according to claim 18.

20. A non-transitory storage medium readable by a computer storing the sleepiness calculation program according to claim 19.

* * * * *